United States Patent [19]

Canzoneri

[11] 4,446,435
[45] May 1, 1984

[54] ULTRASONIC STREAMING CURRENT DETECTOR

[75] Inventor: Anthony S. Canzoneri, Kenner, La.

[73] Assignee: Process Development, Inc., Kenner, La.

[21] Appl. No.: 375,577

[22] Filed: May 6, 1982

[51] Int. Cl.³ .......................................... G01N 27/60
[52] U.S. Cl. .................................. 324/453; 324/447; 324/71.1; 134/1
[58] Field of Search ............... 324/453, 452, 425, 438, 324/439, 444, 445, 447, 450, 71.1; 134/1, 143, 184; 204/193, 280

[56] References Cited

U.S. PATENT DOCUMENTS 3,365,376 1/1968 Weyland .............................. 324/447
3,368,145 2/1968 Gerdes ................................ 324/71.1
3,420,758 1/1969 Scheer ..................................... 134/1

Primary Examiner—Michael J. Tokar
Attorney, Agent, or Firm—Keaty & Keaty

[57] ABSTRACT

An ultrasonic streaming current detector for developing on a continuous basis, electrical signal which is a function of the charge condition existing in the stream containing charged particles therein, for thereby facilitating the determination of the dosage of floculate to be added to a charge implacing species field stream, for thereby ultimately controlling floculation of such streams. The present invention employs a cross-shaped housing having cross-member and a longitudinal member, a piston receiving member, a reciprocating piston, a pair of electrodes, a meter recorder and a electrical mortar. The piston pumps, the simple stream within its interior and by means of this reciprocating shear force against the simple stream generating an electrical signal across electrodes dispositioned at either end of the pump stroke of the piston to thereby generate an electrical signal through lead wires connected to a meter recorder box. The circuitry of the meter recorder box converts the electrical signal into a routable form which is representative of the average electrical charge of the suspended particles in said simple stream.

18 Claims, 6 Drawing Figures

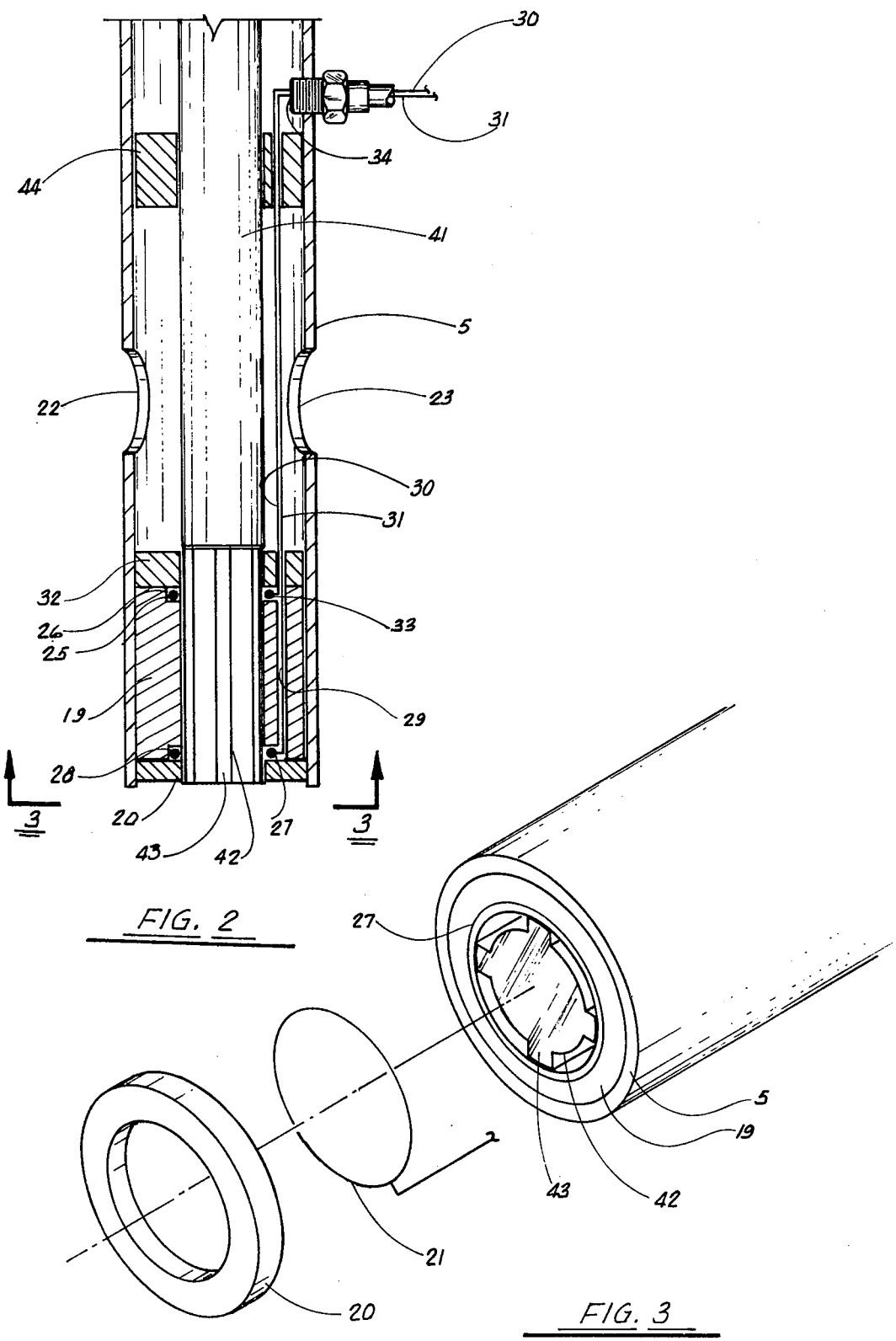

4,446,435

ULTRASONIC STREAMING CURRENT DETECTOR

BACKGROUND OF THE INVENTION

1. Field of the Invention

The present invention relates to an improved apparatus for determining the charge of aqueous suspensions of finely divided, solid, charged particles which determination can be utilized in the continuous regulation of the flocculation of the finely divided charged particles.

2. General Background

It is conventional practive in clarifying aqueous systems containing suspended particles to employ a flocculation operation. Once flocculated, the suspended particles can be separated from their fluid medium by sedimentation, filtration, floatation, centrifugation or one or more of the foregoing physical separatory processes in combination. Conventionally, the flocculation operation is promoted by the use of flocculating chemicals such as alum, ferric chloride or various polymeric materials such as water-soluble cationic and anionic organic polyelectrolytes. Aqueous suspensions of finely divided polymeric particles are encountered in a paper machine headbox within a paper manufacturing process operation and in many other contexts. In a typical flocculation process for flocculating aqueous suspensions of finely divided particles, a water-soluble cationic flocculating chemical is added to the solution. The finely divided particles suspended in the solution are normally negatively charged and thus, the addition of the cationic agent results in charge neutralization on the suspended particles. When the average charge is zero, or some other predetermined value, the dispersed organic and/or inorganic particles undergo flocculation, i.e. aggregation at an optimum rate. Too much cationic agent, however, creates positively charged particles which can be as difficult to flocculate as are the originally negatively charged particles.

To date, however, determining how much chemical to add to the stream to be treated has been difficult, especially since the composition of such stream often varies over fairly wide ranges and time intervals of a few minutes to a few hours.

Various empirical approaches to "finding" the correct dosage of flocculant to be added to a stream have been used. For example, increasing amounts of flocculant may be added to samples from the stream and the amount of decrease in turbidity of the stream noted, the correct dosage being determined as the one which causes the greatest decrease in turbidity with the least addition of flocculant. Such a procedure is time consuming and therefore not really suitable where the composition of the treated solution varies, since the information resulting from this procedure is no longer valid or applicable to the treated solution since the composition of the treated solution will have varied by the time the data has been corrected. The present invention has a built-in early warning system which alleviates this problem.

Another approach is to use a so-called Zeta meter to determine the charge condition existing in the stream. The Zeta meter is used to observe the time required for a charged particle from the stream to pass a predetermined distance along a liquid path while under the influence of an electric field. This method is time consuming and requires a technician to perform the test and to interpret test results before the stream is treated with a greater, lesser, or the same amount of flocculant as had been used since the last previous Zeta meter test was made.

The usual methods of determining the dosage of flocculant to be added to a stream having suspended charge particles are discontinuous and require a substantial amount of individual labor is making the test. The use of such tests in controlling flocculation of such streams is costly both from the standpoint of the labor involved and from the fact that the amount of flocculant actually required by the stream may vary from that indicated by the test.

Accordingly, a principal object of the present invention is to provide an improved instrument which is useful controlling the dosage of chemicals to be added to a controllable stream having a charged condition existing therein.

A further object of the present invention is to provide an improved instrument which is capable of developing, on a continuous basis, an electrical signal which is a function of the charge condition existing in a stream containing charged particles therein.

In accordance with the present invention there is provided a cross-shaped member with a cross-member element and a longitudinal element. Said longitudinal element is provided on its lower end with ingress means for allowing the intake of a sample stream of fluid containing charge-influencing species. The cross-member element is provided with egress means on one end thereof for allowing the outflow of the sample stream. The cross-shaped member is bored through its cross-member and longitudinal elements. A metal tube is disposed in the bore of the longitudinal element of said cross-shaped member, forming a chamber between the outer surface of the metal tube and the inner surface of the longitudinal element. The metal tube extends through the top end of the longitudinal element for mating with a meter/recorder box. A cylindrical, dielectric sleeve is disposed in the bottom of the bore of the metal tube and in fluidly sealing engagement thereto. The dielectric sleeve is adapted for receiving a piston which is connected by a shaft to the inside of the meter/recorder box, the shaft being connected to a rotatable cam driven by an electric motor enclosed by said meter/recorder box. The dielectric sleeve comprises a first ring electrode element in its upper end and a second ring electrode element in its lower end. When turned on, the electric motor inside of the meter/recorder box imparts a torque to said rotatable cam thereby causing said piston to reciprocate within said dielectric sleeve, the stroke of said piston generating a reciprocating shear force against, and thereby generating an electron flow within, a streamed flow of the sample stream which is being pumped or force-fed through said ingress means into the bore of said longitudinal element, through said chamber, and through apertures provided in said metal tube above said dielectric sleeve, and thus, into the bore of said dielectric sleeve. An insulated electrical wire, or first lead wire leads from said first electrode, and a braided shield wire, or second lead wire leads from said second electrode, through a channel provided in said dielectric sleeve and up along the inner surface of said metal tube and through an aperture provided at some arbitrary point near the top of said metal tube, ultimately connecting to circuitry provided in the meter/recorder box. The electron flow generated within the sample stream by the reciprocating shear force of the piston moving up and down within said dielectric sleeve is measured by means of the electrical signal thereby generated across said electrodes travelling through said lead wires, and through the circuitry provided inside of the meter/recorder box. Said circuitry converts said electrical signal into a readable form which is representative of the average electrical charge of the suspended particles in said sample stream.

The present state of the art has advanced to a point similar to the above described apparatus. However, nothing in the prior art has been practically operable due to accumulated particle buildup from the sample stream on the walls of the receiving tube. It is a major objective of the present invention to eliminate this problem which makes these devices impractical to use. The present invention employs an ultrasonic cleaning device which, in accordance with the present invention, is mounted onto the cross-member element of said cross-shaped member on the opposite end thereof from the egress means for said sample stream. Said ultrasonic cleaner which is commercially available, generates mechanical vibrations or shock waves through and around the receiving tube, or dielectric sleeve, thereby preventing particle buildup on the walls thereof. As a result, an accurate determination and reading of the electric potential or charge of the sample stream is facilitated. Further, the present invention employs an optical isolator device inside of the meter/recorder device to facilitate synchronous rectification of the alternating current signal developed across said electrodes. This optical isolator device replaces the magnetically actuated switches employed in the prior art which wear out easier and do not function as well as the optical isolator device of the present invention.

Any additional objects and advantages of the present invention as above briefly described will be best understood when the following detailed description is read in connection with the accompanying drawings, in which:

BRIEF DESCRIPTION OF THE DRAWINGS

FIG. 2 is an elevated, cross-sectional view of the piston as it is contained within the bore of the dielectric sleeve encased by the metal tube.

FIG. 3 is a cross-sectional bottom view of the piston as it is contained within the bore of the dielectric tube encased by the conductive metal tube.

Figure 1:
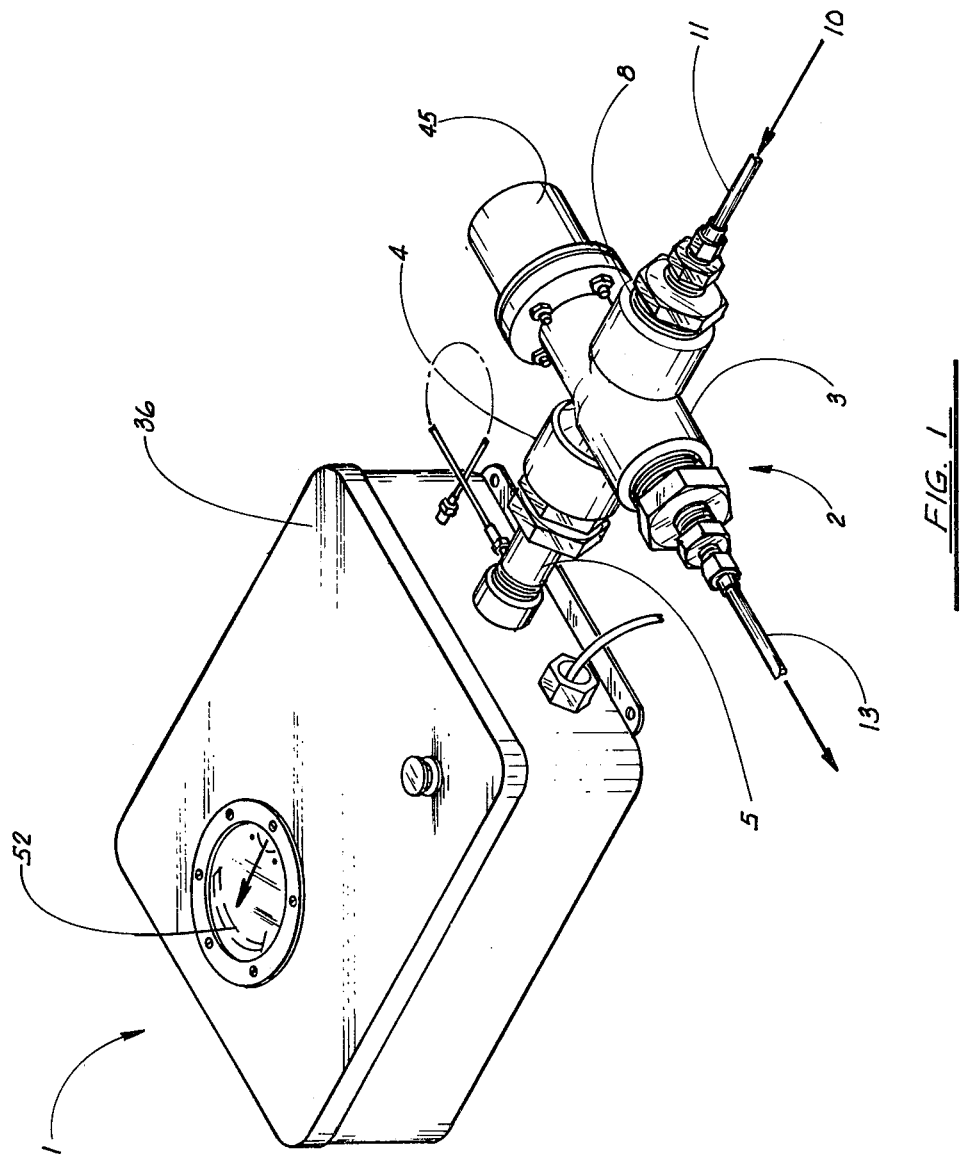
FIG. 1 is a perspective view of the entire apparatus of the present invention.

Referring to the drawings, there is shown apparatus in accordance with the present invention for detecting the average electrical charge density on the dielectric surfaces of an annulus, the charge density being a function of the charge influencing species, such as charged molecules, or colloidal particles, for example, which are present in a liquid stream in flowing contact with said dielectric surface.

Figure 5:
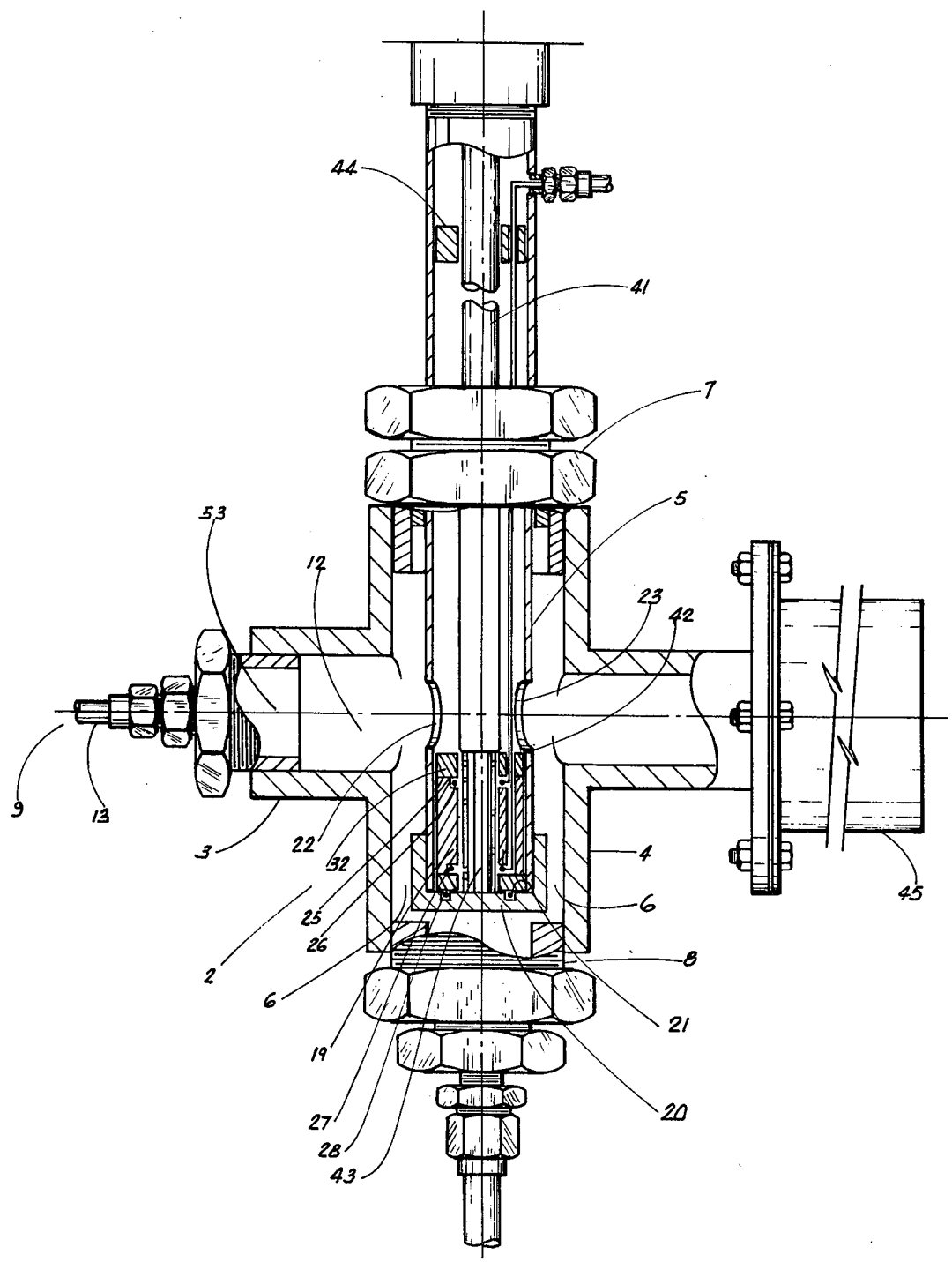
FIG. 5 is an elevated, cross-sectional view of the cross-shaped member.

As seen in FIG. 1, the apparatus, indicated generally by the numeral 1, comprises a small cross-shaped tubular member 2 unitarily comprising a cross-member element 3 and a longitudinal element 4. A metal tube 5, or pipe 5 of at least a smaller diameter than the diameter of the bore of longitudinal element 4 is inserted into the bore of longitudinal element 4 terminating at least a short distance from the lower end of longitudinal element 4. As seen in FIG. 5, a chamber 6 is thereby formed between the outer surface of metal tube 5 and the inner surface of longitudinal element 4. A retainer nut 7 mates cross-shaped member 2 with metal tube 5 above the top end of longitudinal element 4. Longitudinal element 4 is provided with ingress means 8 at its lower end for facilitating the intake of a sample stream of fluid containing charge-influencing species 9 which is pumped or force-fed from a process stream 10 or sample reservoir 10 through any suitable medium, for example, pipe 11, through ingress means 8 and into chamber 6 formed between metal tube 5 and the inner surface of longitudinal element 4. After the sample stream of fluid 9 fills chamber 6 it is held or contained in the bore 12 of cross-member element 3, hereinafter referred to as fluid reservoir 12. Cross-member element 3 is provided with egress means 13 for facilitating the outflow of sample fluid 9 from fluid reservoir 12, egress means 13 being provided at the outer end of one side of cross-member element 3.

Figure 4:
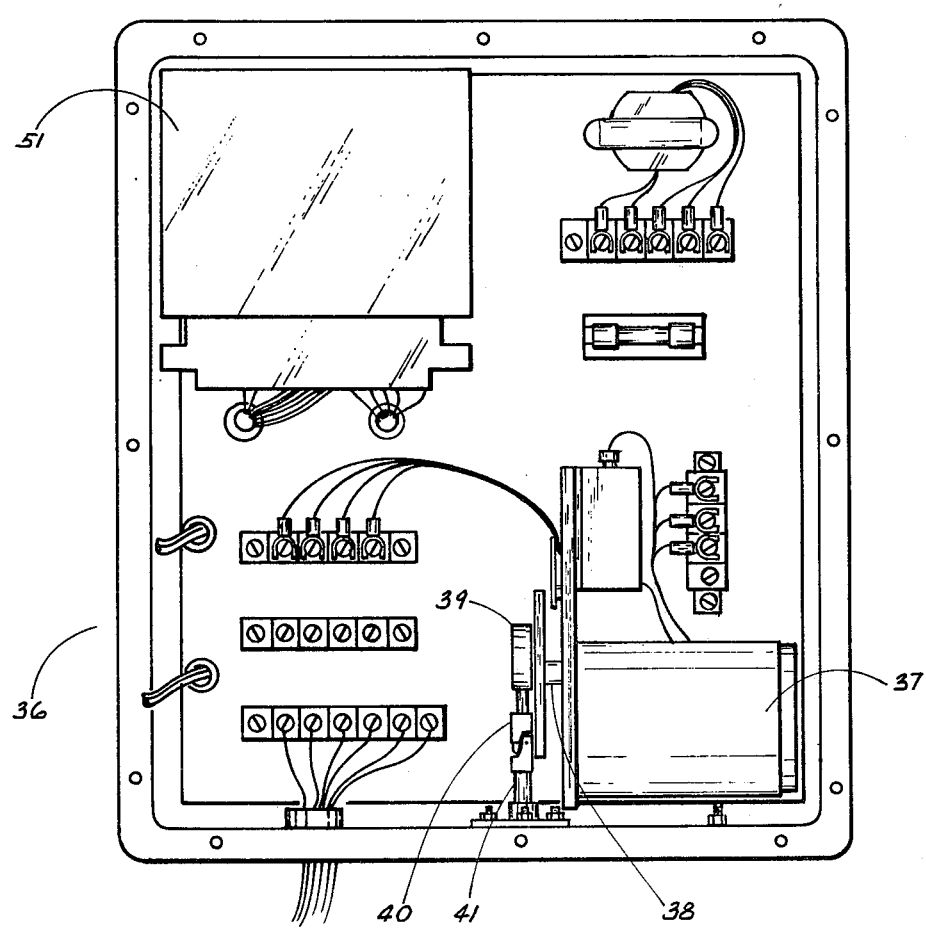
FIG. 4 is a front view of the meter/recorder device having its front plate removed.

A cylindrical, dielectric sleeve 19 is mounted within the bore of said metal tube 5, at its lower end, and in fluidly sealing engagement thereto. A cylindrical, dielectric cap 20 is coupled to the bottom end of metal tube 5, O-ring 21 being inserted therebetween, to ensure a fluid seal between cap 20 and the bottom end of metal tube 5. It is important to note that cap 20 does not block chamber 6. Apertures 22, 23 are provided diametrically opposite each other through the walls of metal tube 5 at least just above cap 20, thereby providing a straight-through, linear fluid flow passage through metal tube 5, for reasons which will hereinafter be seen. A first ring electrode 25 is mounted in a channel 26 provided in the inside perimeter of the top of sleeve 19 and a second ring electrode 27 is mounted in a channel 28 provided in the inside perimeter of the bottom of sleeve 19, so that the two electrodes 25, 27 are in spaced relationship to each other, as best seen in FIG. 2. Dielectric sleeve 19 may be made of glass or other ceramics, polyethylene, polystyrene, nylon, beeswax, paraffin, or polytetrafluoroethylene, for example, or of any other electrically insulating material having suitable dielectric characteristics. As seen in FIG. 2, a channel 29 is provided in sleeve 19, from the bottom through the top thereof. A first lead wire 30 emanates from first electrode 25 through channel 29, first lead wire 30 being circumferentially insulated. A braided shield wire 31, hereinafter referred to as second lead wire 31, similar to an antenna wire, emanates from second electrode 27 through channel 29. A potting material (not shown), for example, epoxy, is injected into channel 29 so as to completely fill channel 29, thereby fluidly sealing channel 29 and securing first and second lead wires 30, 31 in a fixed position therein. A cylindrical, dielectric cap 32 made of any suitable dielectric material, is mated into the top of sleeve 19, by means of any suitable fastening device, such as screws. A channel 33 of the same diameter as channel 29 provided in said sleeve 19 is provided in cap 32, and is perfectly aligned with channel 29 so as to form a single, continuous channel therein. First and second lead wires, 30, 31 emanate from channel 29 in sleeve 19, through channel 33 in cap 32, and travel along the inside walls of metal tube 5, through an aperture 34 provided at some arbitrary point near the top of metal tube 5, ultimately connecting electrodes 25, 27 to circuitry 51 meter/recorder device 36, as seen in FIG. 4. A potting material (not shown), for example epoxy, is injected into channel 33 so as to completely fill channel 33, thereby fluidly sealing channel 33 and securing first and second lead wires 30, 31 in a fixed position therein.

Referring now to FIG. 4, an electric motor 37, which comprises a rotatable shaft 38, is mounted inside of meter/recorder device 36. Rotatable shaft 38 extends through electric motor 37 perpendicularly to longitudinal element 4 of cross-shaped member 2. As seen in FIG. 4, an eccentric cam 39 is coupled to shaft 38 at least approximately at the intersection of shaft 38 with the vertical axis of longitudinal element 4. A universal joint 40 is coupled to eccentric cam 39 on the top end so as to extend vertically downward substantially coincidental with the vertical axis of longitudinal element 4. Connecting rod 41 is linearly coupled to the lower end of universal joint 40 substantially along the same axis (i.e., at an approximately 180° angle thereto). A reciprocating element 42, or piston 42, as seen in FIG. 5, is coupled to the lower end of connecting rod 41. The diameter of piston 42 is such that it fits slidably, 0.005 inches clearance, for example, within the bore of dielectric sleeve 19. Piston 42 is provided with diametrically opposed, longitudinally extending lands 43, as seen in FIGS. 2 and 3. A cross-sectional bottom view of piston 42 as it is contained within the bore of dielectric sleeve 19 within metal tube 5, is shown in FIG. 3. The outer surface of piston 42 may be made of glass or ceramic material, polyethylene, polystyrene, nylon, poltetrafluorethylene, or any other electrically insulating material having suitable dielectric characteristics. Usually, the entire piston 42, rather than just its outer surface, is made of the insulating material. A cylindrical, dielectric sleeve 44, is mounted near the top of the bore of metal tube 5, in fluidly sealing engagement thereto. Sleeve 44 functions as a guide device for connecting rod 41, thereby ensuring that piston 42 remains in at least a substantially vertical axis upon actuation thereof. As seen in FIG. 5, an ultrasonic cleaning device 45, as will be hereinafter discussed, is mounted to the side of crossmember element 3 of cross-shaped member 2 opposite egress means 13.

In operation, electric motor 37 is energized by a suitable source, such as a battery, thereby transmitting torque to rotatable shaft 38, thereby rotating eccentric cam 39, as seen in FIG. 4.

The rotation of eccentric cam 39 causes universal joint 40 to reciprocate, thus moving connecting rod 41 and piston 42 up and down within the bore of dielectric sleeve 19 in a cyclic manner. In one instrument made in accordance with the present invention, piston 42 has a one-inch stroke.

Figure 6:
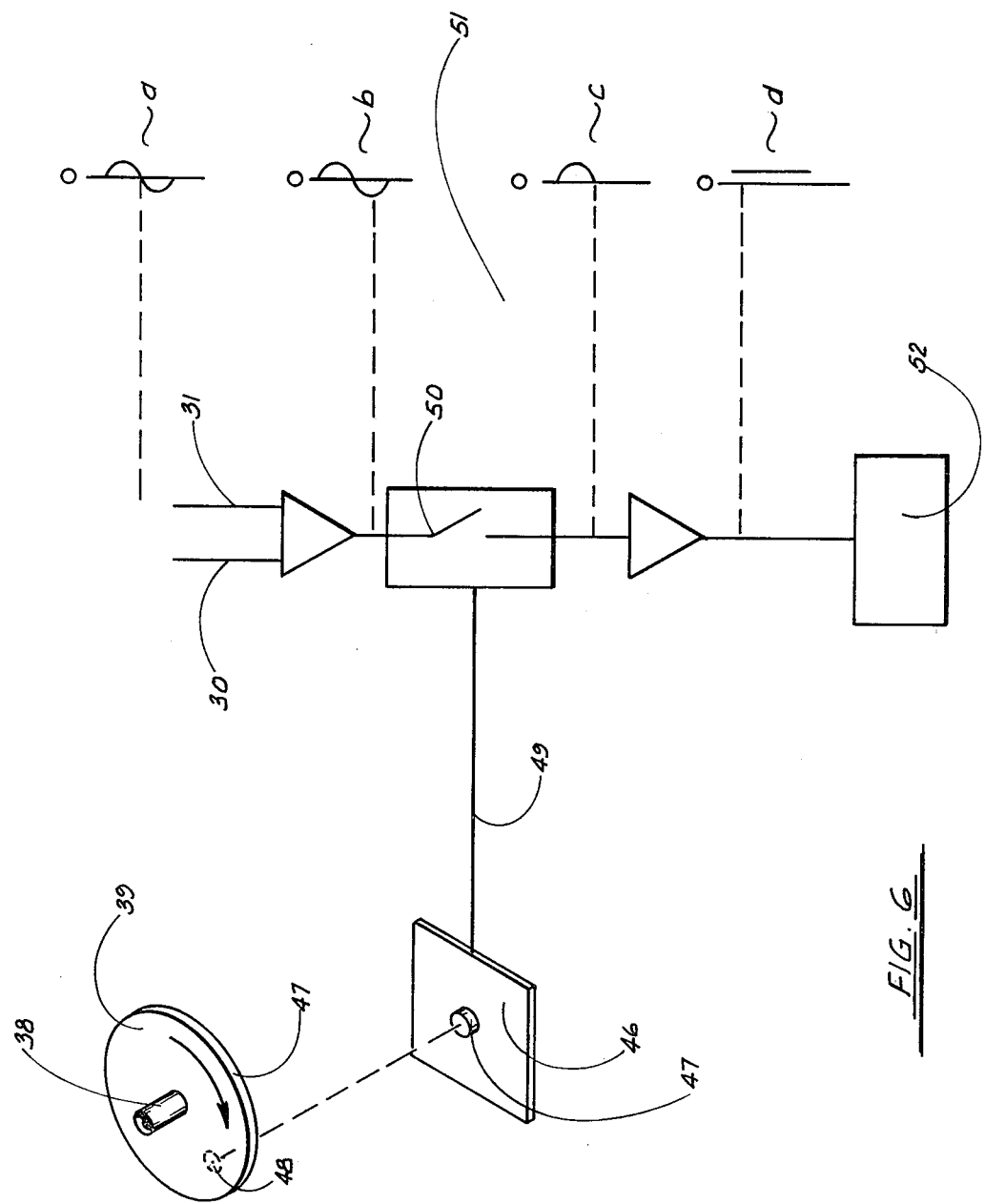
FIG. 6 is a schematic diagram of the optical isolator device in conjunction with the rotatable cam.

Assuming that a sample stream of a fluid material containing charge-influencing species 9, e.g., a polymeric solution emanating from a paper machine headbox of a paper manufacturing plant, to be analyzed (i.e., have its charge characteristics determined) is force-fed or pumped into ingress means 8, the sample stream 9 enters the bore of longitudinal element 4 of cross-shaped member 2, as the diameter of ingress means 8 is at least smaller than the diameter of the bore of longitudinal element 4. The sample stream 9 then flows through chamber 6 and after filling chamber 6 it is held in reservoir 12. Egress means 13 is located approximately on the same imaginary plane as the midpoint of apertures 22, 23 of metal tube 5, as represented by the phantom lines 53 in FIG. 5. By this means, the sample stream 9 will be outflowed from fluid reservoir 12 through egress means 13 when the level of the fluid in fluid reservoir 12 attempts to become higher than approximately the midpoint of apertures 22, 23 of metal tube 5. The offset of eccentric cam 39 is such that the most downward stroke of piston 42 is approximately even with the bottom end of dielectric sleeve 19 and the bottom end of metal tube 5. As piston 42 reciprocates in the bore of dielectric sleeve 19, the sample stream of liquid 9 is ultimately forced, on the upstroke (under some degree of vacuum), through apertures 22, 23 into the bore of dielectric sleeve 19 and forced (under pressure), on the downstroke, out of the bore of dielectric sleeve 19, and through egress means 13 of cross-shaped member 2. The sample stream of fluid 9 is thus ultimately forced into and out of the bore of dielectric sleeve 19, thus generating a streaming smaple fluid flow across electrodes 25, 27, as seen in FIG. 2. An electrical signal which is responsive to the charge, or electric potential, contained by the streaming sample fluid 9, is thus generated through electrodes 25, 27 and lead wires 30, 31, therefore ultimately generating an electrical signal through the circuitry 51 provided on the inside of meter/recorder device 36. The circuitry 51 inside of meter/recorder device 36 is standard and is commercially available. Reference can be had to columns 3, 4, 5 and 6 of U.S. Pat. No. 3,368,145 for a detailed description thereof. The electrical signal detected by electrodes 25, 27 are fed via lead wires 30, 31 to the circuitry 51 inside of meter/recorder device 36. The circuitry 51 inside of meter/recorder device 36 synchronously rectifies the alternating electrical signal fed thereinto from electrodes 25, 27 resulting in a direct current output signal which is phase sensitive and which is accurately representative of the current, potential, or average charge density contained by the sample stream fluid 9, and which is displayed in readable form on the readout device 52 of meter/recorder device 36. In order to rectify the alternating current created across electrodes 25, 27 by the reciprocating shear force of piston 42 against the sample fluid 9 contained in the bore of dielectric sleeve 19, a commutating device synchronized to piston 42 position is required. In the prior art, a mechanical switch was actuated by the cam which drives the piston. The commutating was done by the switch, which was a common cause of the failure of the entire detection apparatus. In accordance with the present invention, an optical isolator 46 is employed. As seen in FIG. 6, the optical isolator 46 is a solid-state electronic device which is mounted opposite the cam 39. Optical isolator 46 comprises light-emitting diode 47 which generates a stream of light onto the surface 47 of eccentric cam 39, opposite optical isolator 46. The surface 47 of eccentric cam 39 opposite optical isolator 46 is provided with a mark 48 which is of a different hue than the remainder of surface 47. Light-emitting diode 47 of optical isolator 46 detects mark 48, which is positioned on the surface 47 of eccentric cam 39 so that it is detected in synchronization with the stroke of piston 42. Upon sensing mark 48, optical isolator 46 generates electrical current through a wire 49, as seen in FIG. 6, to an electronic switch 50 comprised by the circuitry 51, inside of meter/recorder device 36. The closing of switch 50 rectifies the alternating electrical signal being sent from electrodes 25, 27 to the circuitry 51 inside meter/recorder device 36, circuitry 51 further rectifying the alternating electrical signal into a direct current signal and converting it into readable form for display on readout device 52. The wave function of said electrical signals is depicted in FIG. 6 at the different stages a, b, c, d of its conduction, the phantom lines leading from each diagram a, b, c, d depicting the part of circuitry 50, 51 corresponding to each state of the wave function. It should be noted that the circuitry 51 is designed so that the readout device 52 can be preset to 0, before operation of the present invention. In summary, the reciprocating movement of piston 42 within the bore of dielectric sleeve 19 creates a reciprocating shear force which causes an electron flow within the streaming flow of sample fluid 9 and it is this electron flow which is detected by electrodes 25, 27, thus generating an electrical signal which is fed, as above described, into the circuitry 51 inside of meter/recorder device 36 and which is processed by this circuitry 51 to indicate the average charge density existing in the flowing stream of sample fluid 9. Typical sample streams may be raw water, sewage, a latex, oil-water emulsions, paper machine headbox, or simpler water filtration systems.

Up to the present time, no device similar to that embodied by the present invention has been able to achieve accurate readings due to accumulated charged particle buildup within the bore of the sample fluid receiving chamber, which in the present invention, is the bore of dielectric sleeve 19. To prevent any problems of this nature from occurring, an ultrasonic cleaning device 45 is mounted onto the side of cross-member element 3 of cross-shaped member 2 opposite egress means 13. The ultrasonic cleaning device 45 is an electrical device which can be plugged into any conventional electrical outlet. The ultrasonic cleaning device 45 continuously generates ultrasonic shock waves, or mechanical vibrations which prevent any particles, at least some of which may be charged, from agglomerating onto the walls of piston 42 or the bore of dielectric sleeve 19, but rather causes the particles to stay suspended in the sample stream fluid 9. The elimination of agglomeration of the charged particles ensures that all electrical current generated across electrodes 25, 27 and sent via lead wires 30, 31 to circuitry 51 will be accurately representative of the charge condition of the sample stream 9, rather than being altered by the charge condition of agglomerated particles which have built up on piston 42 or the bore of dielectric sleeve 19. Because of the accurate detection of the electrical current by electrodes 25, 27 the ultimate display on readout device 52 will always be accurate. Inaccurate readings have been heretofore impossible to eliminate, as in, for example, the Dow patent, U.S. Pat. No. 3,368,144, et seq. Every time an inaccurate reading would be encountered, within the context of the prior art, the operator of the apparatus would have to turn it off, disassemble it, eliminate the charged buildup, if possible, and reassemble it. This procedure resulted in much wasted time, necessitated shutdown of the system which the apparatus was regulating, and it was very costly. Also, the apparatus became impaired after numerous disassemblies. The present invention eliminates any problems of this nature and facilitates automatic regulation of the flocculating process. It is important to note that the ultrasonic shock waves or electrical vibrations generated by ultrasonic cleaning device 45 do not create any electrical disturbances or turbulence which could result in an inaccurate reading:

What is claimed as invention is:

1. An ultrasonic streaming current detector apparatus for determining a function of a charge condition present in a system containing fluid with charge-influencing species, comprising:
    a. a cross-shaped tubular member having cross-member and longitudinal elements adapted to being substantially filled with said fluid;
    b. a piston receiving member being longitudinally coaxial with said longitudinal element;
    c. a casing substantially surround said piston receiving member;
    d. a pair of electrodes, the first electrode being disposed adjacent the bottom end of said piston receiving member and the second electrode being disposed in said piston receiving member above the first electrode;
    e. a reciprocating piston element disposed in a central bore of said piston receiving member and said casing;
    f. means for reciprocating said reciprocating element within the bore of said piston receiving member, so as to cause said fluid to flow to and from said bore, in a continuous, repetitive manner thereby generating electrical signals across said electrodes;
    g. means for amplifying electrical signals generated across said electrodes, and means for utilizing said amplified signals;
    h. means for conducting said electrical signals generated across said electrodes from said electrodes to said meams for amplifying said electrical signals and said means for utilizing said amplified signals;
    i. means for synchronizing said conduction of said electrical signals with the action of said reciprocating piston element;
    j. an ultrasonic cleaning device disposed adjacent to said piston receiving member and said casing for generating mechanical vibrations to prevent agglomeration of said charge-influencing species contained by said liquid in the area about said electrodes.

2. The apparatus of claim 1, where said longitudinal element of said cross-shaped member is provided at its lower end with ingress means for allowing intake of said fluid into said longitudinal element and wherein said cross-member element of said cross-shaped member is provided at one end with egress means for allowing the outflow of said fluid from said cross-member element; and wherein said piston receiving member and said casing are being disposed in the bore of said longitudinal element, the diameter of the bore of said longitudinal element being at least larger than the combined diameter of the piston receiving member and the casing; and wherein said ultrasonic cleaning device is mounted to the side of said cross-member element opposite said egress means.

3. The apparatus of claim 2, wherein a chamber is formed between the outer surface of said piston receiving member and the inner surface of said longitudinal element for allowing the flow of said fluid therethrough into the bore reservoir of said cross-member element.

4. The apparatus of claim 1, wherein said piston receiving member is made of dielectric material and is shaped as a cylindrical sleeve disposed at the bottom end of said bore of said casing, influidly sealing engagement thereto.

5. The apparatus of claim 4, wherein said dielectric sleeve is provided with a channel from the bottom through the top thereof.

6. The apparatus of claim 1, wherein said first electrode is a ring electrode mounted in a channel provided in the inside perimeter of the top of said dielectric sleeve and said second electrode is a ring electrode mounted in a channel provided in the inside perimeter of the bottom of said dielectric sleeve, so that the two electrodes are mounted in spaced relationship to each other.

7. The apparatus of claim 6, wherein said first electrode is securably mounted in said dielectric sleeve by means of a cylindrical dielectric cap, said dielectric cap being provided with a channel at least as large as the diameter of said channel of said dielectric sleeve, and said channel of said dielectric cap is aligned with said channel in said dielectric sleeve.

8. The apparatus of claim 6, wherein a cylindrical, dielectric cap is coupled to the bottom of said casing, thereby fluidly sealing the bore of said piston receiving member and said casing, and thereby securing said second electrode into the bottom of said dielectric sleeve.

9. The apparatus of claim 1, wherein said electrical signals are conducted from said first electrode by means of an insulated wire, emanating from said first electrode and travelling through said channel in said dielectric sleeve, through said channel in said dielectric cap, of the inside of the bore of said casing, out of an apperture provided in said casing at a point near the top thereof, to be further connecting with said amplification and utilization means provided in said meter device.

10. The apparatus of claim 1, wherein said electrical signals are conducted from said second electrode by means of a braided shield wire, emanating from said second electrode and travelling through said channel in said dielectric sleeve, through said channel in said dielectric cap, of the inside of the bore of said casing out of an apperture provided in said casing at a point near the top thereof, to be further connected with said amplification and utilization means.

11. The apparatus of claim 1, wherein said casing is a metal tube.

12. The apparatus of claim 1, wherein said channel in said dielectric sleeve and said channel in said dielectric cap are completely filled with a potting material, such as epoxy, thereby fluidly sealing said channels and securing said lead wires of said first and second electrodes in a fixed position therein.

13. The apparatus of claim 1, wherein said casing is provided with two apertures diametrically opposite each other through the walls of said casing at least just above said dielectric cap and substantially coincidental with the longitudinal axis of said cross-member element, thereby providing a linear fluid flow passage through said casing, thereby allowing the flow of said sample fluid through said chamber formed between the outer surface of said piston receiving member and the inner surface of said longitudinal element, through said wire reservoir of said cross-member element, and through said apertures of said casing into the bore of said first piston receiving member, and wherein said egress means of said cross-member element is substantially on the same imaginary plane as the midpoint of said apertures, so as to allow the outflow of said fluid when the fluid in said bore reservoir exceeds the height of the midpoint of said apertures of said casing.

14. The apparatus of claim 1, wherein said means for reciprocating said reciprocating element within the bore of said piston receiving member comprises:
 a. an electric motor;
 b. a rotatable shaft comprised by said electric motor and extending through said electric motor perpendicularly to said longitudinal element of said cross-shaped member;
 c. an eccentric cam coupled to said rotatable shaft at least approximately at the intersection of said shaft with the vertical axis of said longitudinal element;
 d. a universal joint connected to said cam;
 e. a connecting rod coupled to said universal joint extending vertically downward substantially coincidental with the vertical axis of said longitudinal element;
 f. the lower end of said connecting rod is coupled to said reciprocating element.

15. The apparatus of claim 1, wherein it further comprises a meter/recorder device coupled to the top end of said casing, said meter/recorder device comprising said means for amplifying electrical signals generated across said electrodes, said means for utilizing said amplified signals, said means for synchronizing said conduction of said electrical signals with the action of said reciprocating piston element, and a readout device for displaying said electrical signals in readable form.

16. The apparatus of claim 1 wherein said reciprocating element is a piston with at least its outer surface made of a dielectric material.

17. The apparatus of claim 16, wherein said piston is provided with at least one pair of diametrically opposed, longitudinally extending lands.

18. The apparatus of claim 1, wherein said electrodes are reversible electrodes.

* * * * *